(12) United States Patent
Bernhardt et al.

(10) Patent No.: US 10,194,877 B2
(45) Date of Patent: Feb. 5, 2019

(54) GENERATING X-RAY PULSES DURING X-RAY IMAGING

(71) Applicants: Philipp Bernhardt, Forchheim (DE); Thomas Ferger, Fürth (DE); Markus Schild, Herzogenaurach (DE); Kai-Uwe Taubenreuther, Schellenberg (DE); Mathias Kraus, Gößweinstein (DE)

(72) Inventors: Philipp Bernhardt, Forchheim (DE); Thomas Ferger, Fürth (DE); Markus Schild, Herzogenaurach (DE); Kai-Uwe Taubenreuther, Schellenberg (DE); Mathias Kraus, Gößweinstein (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/807,700

(22) Filed: Nov. 9, 2017

(65) Prior Publication Data

US 2018/0139829 A1  May 17, 2018

(30) Foreign Application Priority Data

Nov. 15, 2016 (DE) .................. 10 2016 222 365

(51) Int. Cl.
*A61B 6/00* (2006.01)
*H01J 35/04* (2006.01)
(Continued)

(52) U.S. Cl.
CPC .............. *A61B 6/487* (2013.01); *A61B 6/40* (2013.01); *A61B 6/405* (2013.01); *A61B 6/486* (2013.01);
(Continued)

(58) Field of Classification Search
CPC ........... A61B 6/40; A61B 6/405; A61B 6/504; A61B 6/54; A61B 6/542; A61B 6/486;
(Continued)

(56) References Cited

U.S. PATENT DOCUMENTS 4,104,526 A * 8/1978 Albert .................. G01N 23/223
378/106
4,361,901 A * 11/1982 Daniels .................... A61B 6/02
257/10
(Continued)

FOREIGN PATENT DOCUMENTS

CN 104411080 A 3/2015
DE 102009004186 A1 1/2010
(Continued)

OTHER PUBLICATIONS

Chinese First Office Action (translated) for Chinese Application No. 201711129479.9 dated Aug. 30, 2018.*
(Continued)

*Primary Examiner* — Allen C Ho
(74) *Attorney, Agent, or Firm* — Lempia Summerfield Katz LLC

(57) ABSTRACT

Systems and methods are provided for generating X-ray pulses during X-ray imaging. A high voltage of an X-ray tube is automatically switched off. The tube voltage decays and upon reaching a predefined threshold value of the tube voltage or a predefined waiting time after switching off the high voltage, a grating voltage of a grating arranged between an emitter and an anode of the X-ray tube is automatically switched on. No electrons reach the anode from the emitter, and the tube current drops to the value zero.

10 Claims, 3 Drawing Sheets

(51) Int. Cl.
*H01J 35/06* (2006.01)
*H01J 35/10* (2006.01)
*H05G 1/08* (2006.01)
*H05G 1/26* (2006.01)
*H05G 1/28* (2006.01)
*H05G 1/30* (2006.01)
*H05G 1/32* (2006.01)
*H05G 1/34* (2006.01)
*H05G 1/38* (2006.01)
*H05G 1/56* (2006.01)
*H01J 35/08* (2006.01)
*G21K 1/06* (2006.01)

(52) U.S. Cl.
CPC ........... *A61B 6/504* (2013.01); *A61B 6/54* (2013.01); *A61B 6/542* (2013.01); *H01J 35/04* (2013.01); *H01J 35/045* (2013.01); *H01J 35/10* (2013.01); *H05G 1/085* (2013.01); *H05G 1/26* (2013.01); *H05G 1/265* (2013.01); *H05G 1/28* (2013.01); *H05G 1/30* (2013.01); *H05G 1/32* (2013.01); *H05G 1/34* (2013.01); *H05G 1/38* (2013.01); *H05G 1/56* (2013.01); *G21K 1/067* (2013.01); *H01J 35/06* (2013.01); *H01J 35/08* (2013.01)

(58) Field of Classification Search
CPC ........ A61B 6/487; H01J 35/04; H01J 35/045; H01J 35/06; H01J 35/08; H01J 35/10; H05G 1/08; H05G 1/085; H05G 1/26; H05G 1/265; H05G 1/28; H05G 1/30; H05G 1/32; H05G 1/34; H05G 1/56
USPC .................. 378/91, 106, 113, 138, 42
See application file for complete search history.

(56) References Cited

U.S. PATENT DOCUMENTS

| | | | | |
|---|---|---|---|---|
| 5,563,923 A * | 10/1996 | Okada | H01J 35/04 | 378/138 |
| 5,617,464 A * | 4/1997 | Mika | H01J 35/04 | 315/169.1 |
| 6,178,226 B1 * | 1/2001 | Hell | H05G 1/34 | 378/109 |
| 6,215,850 B1 * | 4/2001 | Blake | H05G 1/32 | 378/101 |
| 6,333,968 B1 * | 12/2001 | Whitlock | B82Y 10/00 | 378/122 |
| 6,385,294 B2 * | 5/2002 | Suzuki | H01J 5/52 | 378/121 |
| 6,553,096 B1 * | 4/2003 | Zhou | A61B 6/4028 | 378/122 |
| 6,570,958 B2 * | 5/2003 | Brendler | H01J 35/045 | 378/113 |
| 6,807,248 B2 * | 10/2004 | Mihara | A61B 6/032 | 378/10 |
| 6,816,573 B2 * | 11/2004 | Hirano | G01N 23/04 | 363/17 |
| 6,876,724 B2 * | 4/2005 | Zhou | A61B 6/032 | 378/119 |
| 6,882,703 B2 * | 4/2005 | Price | H01J 35/065 | 378/101 |
| 6,944,268 B2 * | 9/2005 | Shimono | H01J 35/045 | 378/111 |
| 7,133,495 B2 * | 11/2006 | Nakamura | H05G 1/10 | 378/114 |
| 7,151,818 B1 * | 12/2006 | Hanington | H05G 1/10 | 378/104 |
| 7,215,739 B2 * | 5/2007 | Cunningham | H05G 1/30 | 378/112 |
| 7,227,924 B2 * | 6/2007 | Zhou | A61B 6/032 | 378/10 |
| 7,286,642 B2 * | 10/2007 | Ishikawa | H05G 1/46 | 378/109 |
| 7,406,154 B2 * | 7/2008 | Resnick | A61B 6/032 | 378/113 |
| 7,440,547 B2 * | 10/2008 | Ishiyama | A61B 6/032 | 378/101 |
| 7,460,635 B2 * | 12/2008 | Fujimoto | A61B 6/032 | 378/16 |
| 7,529,344 B2 * | 5/2009 | Oreper | H01J 35/045 | 378/134 |
| 7,649,974 B2 * | 1/2010 | Arenson | A61B 6/542 | 378/16 |
| 7,792,241 B2 * | 9/2010 | Wu | H01J 35/045 | 378/114 |
| 7,826,594 B2 * | 11/2010 | Zou | H01J 1/30 | 378/10 |
| 8,295,442 B2 * | 10/2012 | Caiafa | H01J 35/10 | 378/137 |
| 8,300,768 B2 * | 10/2012 | Hashimoto | A61B 6/032 | 378/121 |
| 8,311,186 B2 * | 11/2012 | Perkins | H01J 1/28 | 315/504 |
| 8,320,521 B2 * | 11/2012 | Zou | H01J 35/045 | 378/106 |
| 8,340,250 B2 * | 12/2012 | Lemaitre | A61B 6/032 | 378/122 |
| 8,358,741 B2 * | 1/2013 | Grasruck | H01J 35/045 | 378/113 |
| 8,396,185 B2 * | 3/2013 | Zou | A61B 6/032 | 378/112 |
| 8,401,151 B2 * | 3/2013 | Frontera | H01J 35/14 | 378/136 |
| 8,422,627 B2 * | 4/2013 | Kappler | G01T 1/24 | 378/19 |
| 8,447,013 B2 * | 5/2013 | Sprenger | H01J 35/04 | 378/122 |
| 8,472,585 B2 * | 6/2013 | Ogura | H01J 35/08 | 378/111 |
| 8,498,380 B2 * | 7/2013 | Behling | H01J 35/04 | 378/138 |
| 8,537,965 B2 * | 9/2013 | Dafni | A61B 6/032 | 378/4 |
| 8,625,743 B1 * | 1/2014 | Caiafa | H05G 1/52 | 378/112 |
| 8,675,817 B2 * | 3/2014 | Ogata | H01J 35/045 | 378/101 |
| 8,693,638 B2 * | 4/2014 | Dafni | A61B 6/032 | 378/124 |
| 8,712,015 B2 * | 4/2014 | Caiafa | H01J 35/18 | 378/110 |
| 8,774,364 B2 * | 7/2014 | Aoki | H01J 35/045 | 378/104 |
| 8,774,366 B2 * | 7/2014 | Walk | H05G 1/58 | 378/112 |
| 9,014,336 B2 * | 4/2015 | Luerkens | H05G 1/10 | 378/106 |
| 9,058,958 B2 * | 6/2015 | Aoki | H01J 35/04 | |
| 9,064,670 B2 * | 6/2015 | Kim | H01J 3/021 | |
| 9,072,154 B2 * | 6/2015 | Wang | H05G 1/10 | |
| 9,142,381 B2 * | 9/2015 | Onken | H01J 35/045 | |
| 9,155,185 B2 * | 10/2015 | Reijonen | H01J 35/04 | |
| 9,160,325 B2 * | 10/2015 | Caiafa | H03K 17/04 | |
| 9,224,572 B2 * | 12/2015 | Frontera | H01J 35/045 | |
| 9,253,864 B2 * | 2/2016 | Caiafa | H05G 1/50 | |
| 9,412,552 B2 * | 8/2016 | Aoki | H01J 35/08 | |
| 9,448,327 B2 * | 9/2016 | Perkins | H01J 35/045 | |
| 9,484,179 B2 * | 11/2016 | Frontera | H01J 35/14 | |
| 9,517,043 B2 * | 12/2016 | Tamura | A61B 6/025 | |
| 9,577,766 B2 * | 2/2017 | Zhao | H01J 31/49 | |
| 9,589,759 B2 * | 3/2017 | Miyaoka | H01J 37/16 | |
| 9,673,592 B2 * | 6/2017 | Dittrich | H01T 4/08 | |
| 9,728,367 B2 * | 8/2017 | Park | H01J 35/06 | |
| 9,779,907 B2 * | 10/2017 | Canfield | H01J 35/045 | |
| 9,793,084 B2 * | 10/2017 | Reijonen | H01J 35/04 | |

(56) References Cited

U.S. PATENT DOCUMENTS 9,842,720 B2 * 12/2017 Berk .................... H05G 1/06
9,856,722 B2 * 1/2018 Dong .................... E21B 43/128
2011/0038460 A1 2/2011 Grasruck et al.

FOREIGN PATENT DOCUMENTS

DE 102009037688 A1 3/2011
DE 102009037688 B4 6/2011
DE 10 2016 222 365 B3 * 4/2018 ............... H05G 1/32

OTHER PUBLICATIONS

German Office Action for related German Application No. 10 2016 222 365.8 dated Aug. 18, 2017, with English Translation.
Chinese Office Action for Chinese Application No. 201711129479.9, dated Aug. 30, 2018.

\* cited by examiner

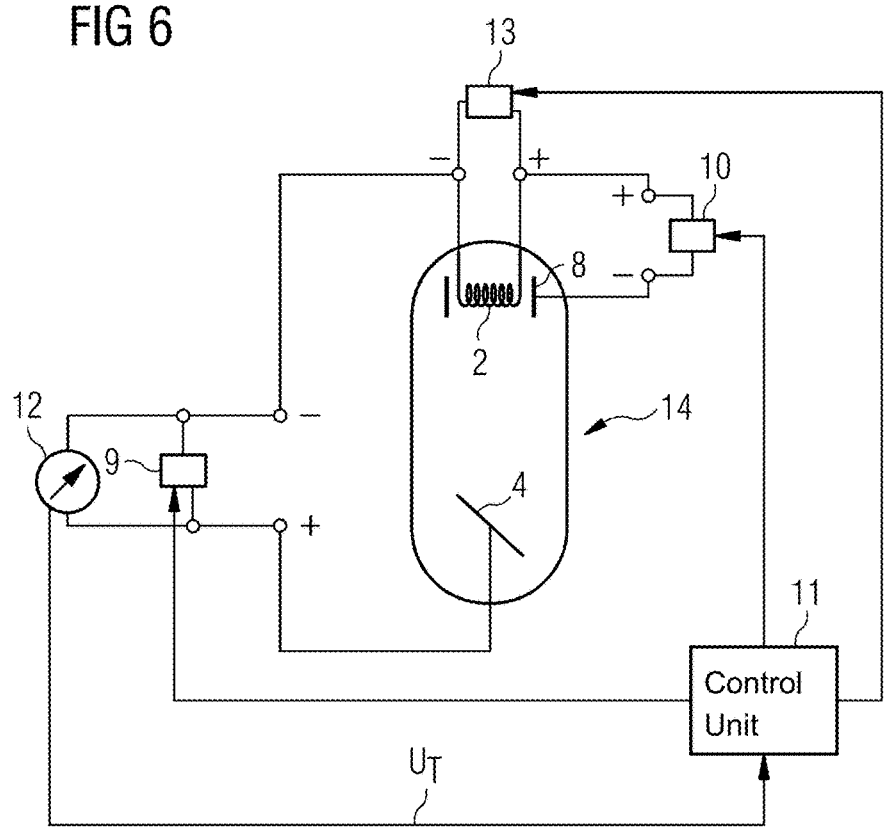

GENERATING X-RAY PULSES DURING X-RAY IMAGING

CROSS REFERENCE TO RELATED APPLICATION

This application claims the benefit of DE 102016222365.8, filed on Nov. 15, 2016, which is hereby incorporated by reference in its entirety.

FIELD

Embodiments relate to a method, a computer program product, a computer-readable medium and an apparatus for generating X-ray pulses during X-ray imaging.

BACKGROUND

In X-ray-based imaging, X-ray emitters may be used as a particle source. Often, the X-ray emitters are pulsed in order, for example, to keep the patient dose low during medical imaging. The configuration of a known X-ray emitter or X-ray tube is depicted in FIG. 1.

FIG. 1 depicts a cross-section of an X-ray emitter. In a vacuum tube 1, electrons 3 are released into the vacuum by heating an emitter 2 (e.g. cathode). The electrons 3 are accelerated towards the anode 4 by a high voltage, that is applied between the emitter 2 and an anode 4. Upon striking the anode 4, approximately 1% of the energy of the electrons 3 is converted into X-ray radiation 5, the remaining energy transitioning into heat. The generated heat must be continuously extracted from the anode 4, otherwise there is a risk of the focal path melting on the anode 4. Therefore, in heavy-duty tubes, rotating anodes may be used in combination with directly cooled bearings. The X-ray radiation 5 exits the vacuum tube 1 through the outlet window 6. Using the motorized drive 7, the anode 4 is set in rotation.

For angiography, for example, a pulsed X-ray radiation is used to reduce the X-ray radiation exposure of the patient. The pulse generation for X-ray tubes may be realized by two methods.

A simple method is to switch the high voltage applied between the emitter 2 and the anode 4 on and off (primary pulsed X-ray radiation 5). Alternatively, a grating 8 may be arranged between the emitter 2 and the anode 4, or a metal element may be arranged around the emitter 2, that is exposed to a pulsed blocking voltage, and the electrons 3 are shielded toward the high voltage field. The grating 8 is switched on and off. The grating 8 alternately blocks and guides secondary pulsed X-ray radiation.

The first method is simple to realize. However, high capacities through cables etc. include disadvantage when actuating that the high capacities must be discharged via the X-ray tube causing electrons 3 to briefly strike the anode 4 with a lower energy, having experienced a lower acceleration voltage. The lower-energy electrons 3, however, generate a lower-energy X-ray radiation 5 that, in medical imaging for example, causes unnecessarily high patient doses without contributing to the imaging.

The second method creates clean X-ray pulses limited in terms of time, since the tube current are shielded in a very short switching time. A grating arrangement is disclosed by way of example in patent application DE 10 2009 004 186 A1. In heavy-duty X-ray tubes, however, the tube currents are very high. In order to generate such high tube currents, large emission surfaces of the emitter 2 are helpful. Large emission surfaces, however, are difficult to block. To this extent, a secondary pulsing is difficult in X-ray tubes with large currents.

SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide a method, a computer program product, a computer-readable medium and an apparatus for generating X-ray pulses during X-ray imaging. Embodiments provide that cleanly dispersed X-ray pulses may be generated even with high tube currents.

The high voltage of the X-ray tube is switched off. The high voltage decays rapidly with the strong currents in the X-ray tube.

As soon as the tube voltage has reached a threshold value, at which the emitter may be completely separated from the high voltage in terms of time by a grating, the grating is activated. The applied high voltage then remains at that value.

High currents may be used, while the lower-energy radiation that is undesirable in medical imaging is prevented.

In an embodiment, a method is provided for generating X-ray pulses during X-ray imaging. The high voltage of an X-ray tube is automatically switched off. The tube voltage decays. Upon reaching a predefined threshold value of the tube voltage or a predefined waiting time after switching off the high voltage, the grating voltage of a grating arranged between the emitter and the anode of the X-ray tube is automatically switched on. No electrons reach the anode from the emitter and the tube current drops to the value zero.

Embodiments allow for both high tube currents to be switched and lower-energy X-ray radiation to be prevented.

In an embodiment, the threshold value or the waiting time may be selected such that the emitter may be completely separated from the high voltage by the grating.

In a further embodiment, the threshold value or the waiting time may be determined experimentally or computationally.

Embodiments further provide a computer program product, including a computer program. The computer program may be loaded into a memory device of a control unit. The computer program may be used to carry out acts the method when the computer program is executed on the control unit.

Embodiments also provide a computer-readable medium, on which a computer program is stored. The computer program may be loaded into a memory device of a control unit. The computer program may be used to carry out the acts of the method when the computer program is executed on the control unit.

Embodiments further provide an apparatus for generating X-ray pulses during X-ray imaging. The apparatus includes an X-ray tube, a high voltage generation unit, a grating, a grating voltage generation unit, and a control unit. The X-ray tube includes an emitter and an anode. The high voltage generation unit is configured to build a high voltage between the emitter and the anode. The grating is located between the emitter and the anode and is configured to deflect the electrons of the emitter when a grating voltage is applied. The grating voltage generation unit is configured to build the grating voltage. The control unit is configured to automatically switch off the high voltage of the high voltage supply unit and, upon reaching a predefined threshold value of the tube voltage or a predefined waiting time after switching off the high voltage, to automatically switch on the grating voltage of the grating voltage generation unit.

In an embodiment, the apparatus includes a tube voltage measuring unit electrically connected to the control unit that is configured to calculate the tube voltage of the X-ray tube and transfer the tube voltage to the control unit.

BRIEF DESCRIPTION OF THE FIGURES

FIG. 6 depicts a block diagram of an apparatus for generating X-ray pulses according to an embodiment.

DETAILED DESCRIPTION

Figure 1:
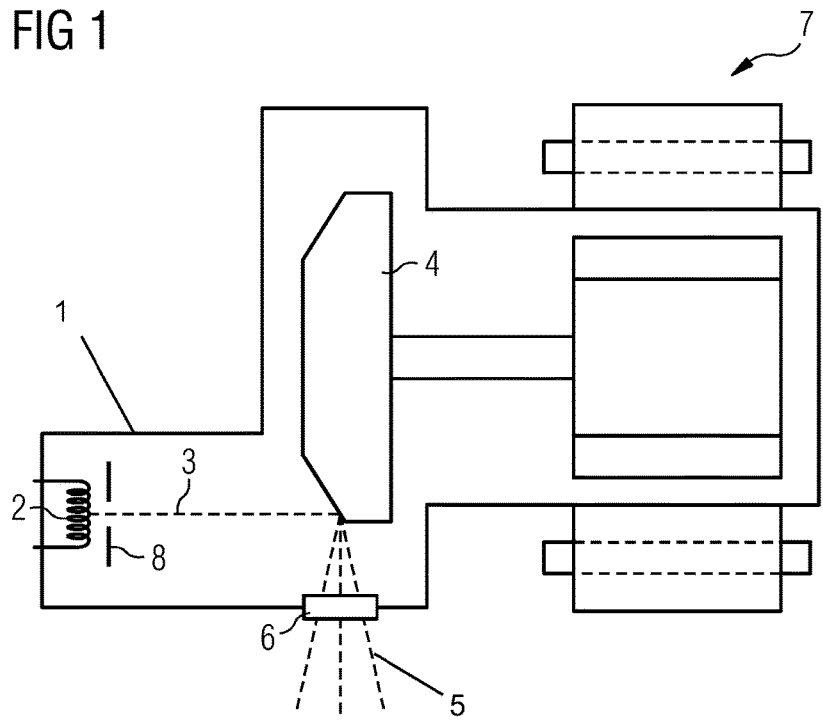
FIG. 1 depicts a cross-section of an X-ray tube.
Figure 2:
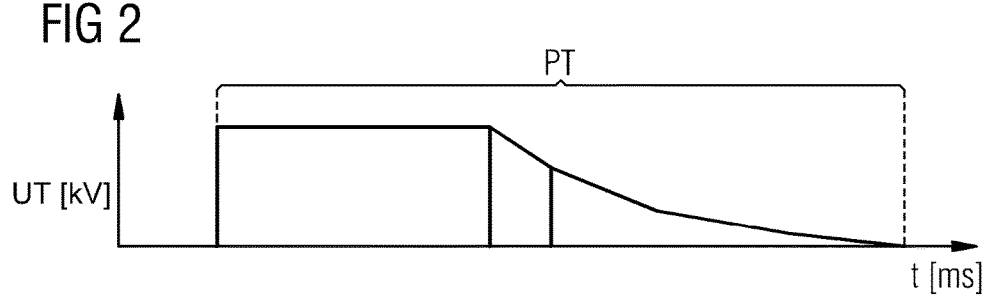
FIG. 2 depicts a tube voltage UT in kV as a function of time in ms for a primary pulsed X-ray radiation according to an embodiment.

FIG. 2 depicts exemplary tube voltage $U_T$ in kV as a function of time t in ms for a primary pulsed X-ray radiation in a graph. After the pulse duration PT, the high voltage is switched off, and the tube voltage drops to the value zero after some time.

Figure 3:
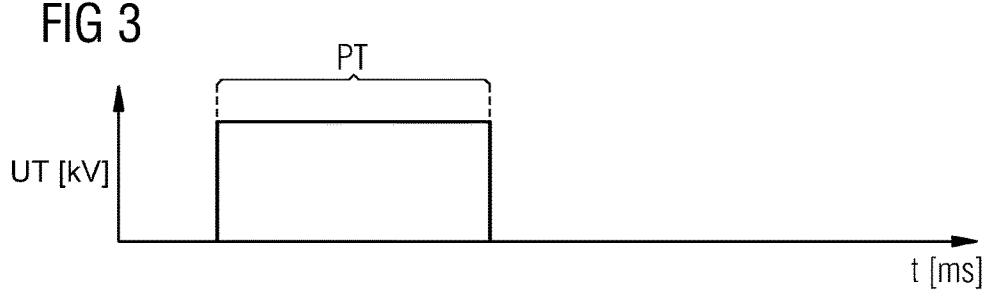
FIG. 3 depicts a tube voltage UT in kV as a function of time in ms for a secondary pulsed X-ray radiation according to an embodiment.

FIG. 3 depicts exemplary tube voltage UT in kV as a function of the time t in ms for a secondary pulsed X-ray radiation in a graph. After the pulse duration PT, a grating voltage is switched on, and tube current IT immediately drops to the value zero, since no further electrons 3 may now reach the anode 4 from the emitter 2. The drop only happens, however, if the tube current or the tube voltage UT is not too great, as only then is the grating 8 fully effective and all electrons may be blocked. The X-ray pulse is cut off cleanly, as depicted in FIG. 3.

Figure 4:
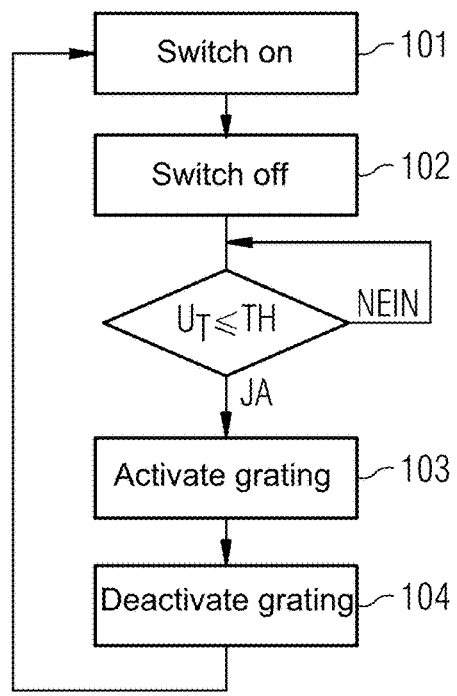
FIG. 4 depicts a flow diagram of an embodiment.

FIG. 4 depicts a flow diagram of one embodiment of a method for generating an X-ray pulse during X-ray imaging. In act 101, the high voltage of the X-ray tube is switched on. In act 102, the high voltage is switched off after the pulse duration PT has expired. Once the tube voltage UT has reached the threshold value TH, the grating 8 is activated in act 103. The tube current IT drops to the value zero. After a pause, in act 104 the grating 8 is deactivated, and the method jumps again to act 101.

Figure 5:
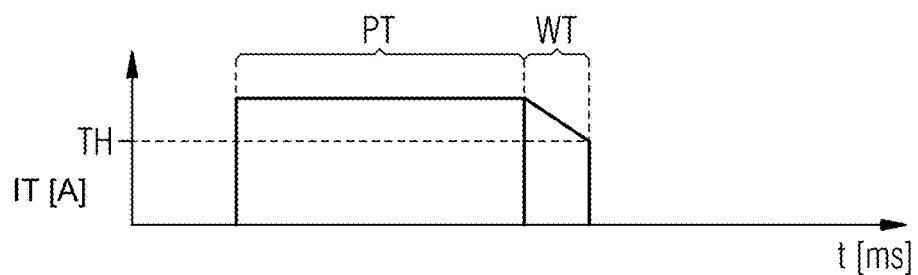
FIG. 5 depicts a tube current IT in A as a function of time in ms according to an embodiment.

The method results in a graph according to FIG. 5. The tube current IT in A is depicted as a function of the time t in ms. The high voltage is switched off after the pulse duration PT and, when the tube voltage UT has reached the threshold value TH, the grating 8 is activated by switching on the grating voltage and the tube current IT drops to the value zero. The resulting pulse duration is therefore composed of the pulse duration PT and the waiting time WT. Only high-energy quanta are generated, although the quanta also travel with large tube currents.

FIG. 6 depicts a block diagram of an apparatus for generating an X-ray pulse during X-ray imaging. The emitter 2 of an X-ray tube 14 is made to anneal with a heating voltage generation unit 13. The high voltage of the high voltage generation unit 9 is applied between the emitter 2 and the anode 4. The grating 8 is powered by the grating voltage generation unit 10. With the aid of the tube voltage measuring unit 12, the tube voltage $U_T$ may be measured. The aforementioned components are controlled by a control unit 11 (e.g., a controller).

The current tube voltage $U_T$ is supplied to the control unit 11 by the tube voltage measuring unit 12. When the previously calculated threshold value TH of the tube voltage $U_T$ is reached, the grating 8 is activated via the control unit 11. Alternatively, after a previously calculated waiting time WT, the grating 8 may be activated. The tube current no longer flows. The X-ray pulse is cut off cleanly. Subsequently, the grating 8 is deactivated, and the high voltage is switched on again.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating X-ray pulses during X-ray imaging, the method comprising:
    automatically switching off a high voltage of an X-ray tube, wherein a tube voltage of the X-ray tube decays; and
    automatically switching on a grating voltage of a grating arranged between an emitter and an anode of the X-ray tube when a predefined threshold value of the tube voltage or a predefined waiting time after switching off the high voltage is reached,
    wherein no electrons reach the anode from the emitter, and a tube current of the X-ray tube drops to the value zero.

2. The method of claim 1, further comprising selecting the predefined threshold value and the predefined waiting time so that the emitter is completely separable from the high voltage in terms of time by the grating.

3. The method of claim 2, further comprising:
    determining the predefined threshold value or the predefined waiting time experimentally or computationally.

4. The method of claim 1, further comprising:
    determining the predefined threshold value or the predefined waiting time experimentally or computationally.

5. In a non-transitory computer readable storage medium that stores instructions executable by one or more processors to generate X-ray pulses during X-ray imaging, the instructions comprising:
    automatically switching off a high voltage of an X-ray tube, wherein a tube voltage of the X-ray tube decays; and
    automatically switching on a grating voltage of a grating arranged between an emitter and an anode of the X-ray tube when a predefined threshold value of the tube voltage or a predefined waiting time after switching off the high voltage is reached, wherein no electrons reach the anode from the emitter, and a tube current of the X-ray tube drops to the value zero.

6. The non-transitory computer readable storage medium of claim 5, wherein the instructions further comprise selecting the predefined threshold value and the predefined waiting time so that the emitter is completely separable from the high voltage in terms of time by the grating.

7. The non-transitory computer readable storage medium of claim 6, wherein the instructions further comprise determining the predefined threshold value or the predefined waiting time experimentally or computationally.

8. The non-transitory computer readable storage medium of claim 5, wherein the instructions further comprise determining the predefined threshold value or the predefined waiting time experimentally or computationally.

9. An apparatus for generating X-ray pulses during X-ray imaging, the apparatus comprising:

an X-ray tube comprising an emitter and an anode;

a high voltage generation unit configured to build a high voltage between the emitter and the anode;

a grating located between the emitter and the anode, the grating configured to block electrons of the emitter from the anode when a grating voltage is applied;

a grating voltage generation unit configured to build the grating voltage; and a controller configured to automatically switch off the high voltage of the high voltage generator and automatically switch on the grating voltage of the grating voltage generator when a predefined threshold value of a tube voltage or a predefined waiting time after switching off the high voltage is reached.

10. The apparatus of claim 9, further comprising:

a tube voltage measuring unit electrically connected to the controller and configured to calculate the tube voltage of the X-ray tube and transfer the tube voltage to the controller.

* * * * *